United States Patent [19]

Brown

[11] Patent Number: 4,987,899
[45] Date of Patent: Jan. 29, 1991

[54] APPLANATION TONOMETER

[76] Inventor: Alan W. Brown, 4 Hartley Cir., Apt. 824, Owings Mills, Md. 21117

[21] Appl. No.: 422,476

[22] Filed: Oct. 17, 1989

[51] Int. Cl.$^5$ .................................. A61B 3/16
[52] U.S. Cl. ..................... 128/645; 128/652
[58] Field of Search ............... 128/645, 646, 647, 652; 351/214

[56] References Cited

U.S. PATENT DOCUMENTS

| | | | |
|---|---|---|---|
| 3,070,997 | 1/1963 | Papritz et al. | 128/652 |
| 3,449,945 | 6/1969 | Mohrman | 128/652 |
| 3,470,736 | 10/1969 | Bartfay | 128/652 |
| 3,924,336 | 12/1975 | Inoue | 33/164 R |

Primary Examiner—Randall L. Green
Assistant Examiner—Randy Shay
Attorney, Agent, or Firm—Diller, Ramik & Wight

[57] ABSTRACT

A split lamp applanation tonometer includes a tonometer tip for contacting a corneal surface of an eye, a mechanism for moving the tonometer tip to applanate and vary the degree of applanation of the corneal surface, an optical viewing axis along which the applanated corneal surface can be viewed, and an electrical and/or optical system for transforming the degree of applanation to an ocular pressure value and displaying the ocular pressure value at a location at which it is visible when a user views along the optical viewing axis whereby both the applanated corneal surface and the ocular pressure value thereof can be viewed simultaneously.

12 Claims, 3 Drawing Sheets

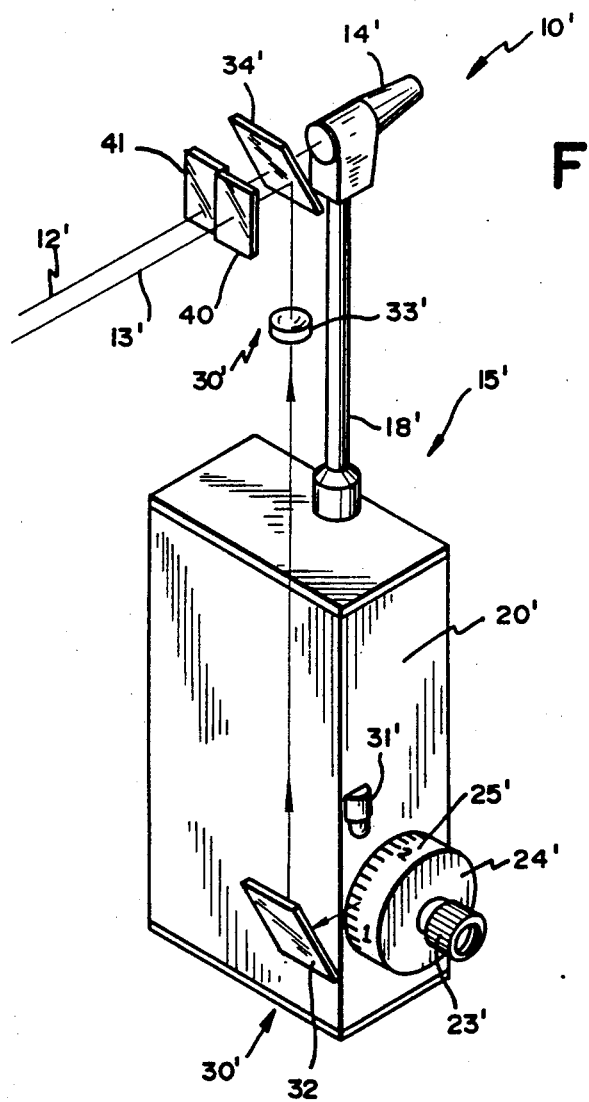
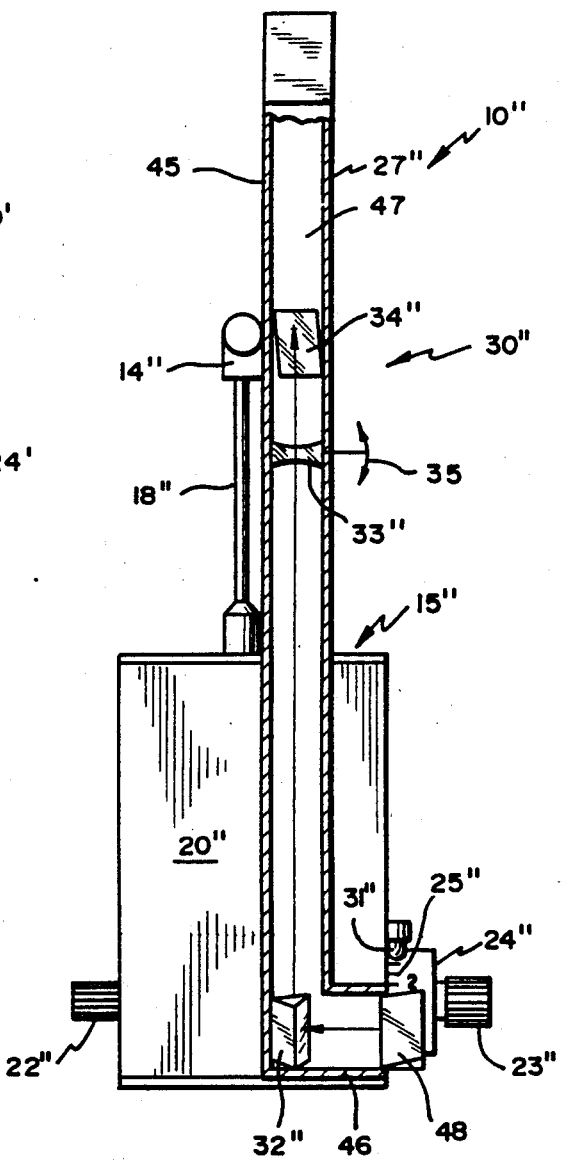
FIG. 3
FIG. 4

APPLANATION TONOMETER

BACKGROUND OF THE INVENTION

The present invention relates to an applanation tonometer for measuring the tonometric or intraocular pressure of an eye by applanation of its cornea. It is clinically important for the ophthalmologist to be able to accurately measure the intraocular pressure of a patient's eye in order to screen and treat various forms of potentially blinding conditions ranging from glaucoma to ocular hypoteny. The principals of applanation tonometry, as presented by Goldman, are the basis for almost all modern slit lamp tonometers which are constructively based upon and utilize the fact that pressure is equal to force multiplied by area. In applanation tonometry, force is applied via a small tonometer tip to a surface of the cornea until the force is sufficient to flatten a known area of the corneal surface. The area of the tonometer tip is designed such that the required force in dynes multiplied by ten is equal to the intraocular pressure in millimeters of mercury. The area used is 3.06 mm. and is achieved as an end point by utilizing a fluorescein stained tear layer under blue cobalt light illumination to highlight the compressed area of the cornea. Under these conditions, the area of the cornea that is compressed is dark blue while the tea layer immediately surrounding the tonometer tip compression is highlighted bright green. The diameter of the circular tonometer tip is set optically via a prism in the tip which splits the highlighted circular area into two overlapping semicircles. A force varying knob of the tonometer is adjusted until the resultant bright green semicircles are partially overlapped.

The tonometer tip is viewed through one-half of the a slit lamp bimicroscope of the slit lamp tonometer and, once properly applanated, is withdrawn from the surface of the cornea by moving the entire slit lamp assembly away from the patient. A force/pressure scale of the tonometer is then read independently of the optics of the slit lamp by the operator gazing down at the force/pressure scale which appears on one of the force varying knobs of the tonometer. A typical applanation tonometer of the type just described is disclosed in U.S. Pat. No. 3,470,736 issued to Stephen A. Bartfay on Oct. 7, 1969 and entitled OCULAR TONOMETER and in U.S. Pat. No. 3,070,997 issued to Franz Papritz et al. on Jan. 1, 1963 and entitled APPARATUS FOR MEASURING THE INTRA-OCULAR OR TONOMETRIC PRESSURE OF AN EYE. The content of the latter-noted two patents is totally incorporated hereat by reference.

Arrangements of the type just described and disclosed in the latter-identified patents is inconvenient because they require the intraocular pressure measurement to be made in two steps for each eye. The operator/user must first align the two semicircles and then withdraw the instrument to read the resulting pressure value from the force/pressure scale of the tonometer force applying knob. Not only must this be done twice, once for each eye, but the process is further compromised because dim ambient lighting conditions are required to observe the semicircles under blue cobalt light illumination, and such dim ambient lighting conditions make the subsequent reading of the unilluminated force/pressure scale difficult with attendant built-in inaccuracies.

SUMMARY OF THE INVENTION

In keeping with the foregoing, the present invention is directed to a novel applanation tonometer which is so constructed and arranged that intraocular pressure can be measured by a single step or procedure associated with each eye, and in accordance therewith the opthalmologist simultaneously views both the two semicircles and the ocular pressure value(s) representative thereof without instrument withdrawal and irrespective of dim ambient lighting conditions.

In keeping with the latter, the present invention is specifically directed to a slit lamp tonometer utilizing a bimicroscope, although the same is equally applicable to an applanation tonometer utilizing a (single) microscope. Most present day applanation tonometers utilize only one-half of the slit lamp bimicroscope to view the corneal surface through the tonometer tip. The other half of the bimicroscope receives only a small rim of light reflected off the tonometer tip or is partially blocked by an associated support arm which is used to hold certain tonometers. Thus, in the past one optical axis of the slit lamp bimicroscope was used to view the corneal surface and the other optical axis was not utilized.

The present invention utilizes the second unused optical axis of the bimicroscope by introducing at the focal plane thereof the image of the force/pressure scale either optically and/or electronically. With this arrangement one eye of the operator/user will be able to view the compressed corneal surface and the associated semicirculars while the other eye of the operator/user simultaneously views the ocular pressure value(s). Thus, as the corneal surface is being compressed the operator/user in a single step operation both simultaneously views the compressed corneal surface and views the ocular pressure of the eye. Obviously, the latter not only involves a single step operation associated with each eye, but it is also independent of the dim ambient room light required for the procedure.

In further accordance with this invention the applanation tonometer uses mirrors and/or prisms to optically translate, transmit and display the ocular pressure value at the focal plane and/or along the second or normally unused optical viewing axis of the bimicroscope. In lieu of mirrors and/or prisms or in association therewith, another embodiment of the applanation tonometer of this invention utilizes fiberoptics and/or an internal reflection system to achieve the latter-defined simultaneous corneal surface and ocular pressure value viewing. In accordance with a third embodiment of an applanation tonometer of this invention, the tonometer force-varying knob, which conventionally has pressure values thereon, is electronically sensed during rotary movement to effect corresponding digital pressure value numerical readouts at the focal plane of the heretofore unused half of the bimicroscope. In each of the latter-described embodiments, the present invention can be constructed as an integral part of a tonometer or as an external adaptation to an existing tonometer and/or the supporting arm and microscope or bimicroscope thereof. Furthermore, all embodiments of the applanation tonometers of the present invention include variable self-illumination systems for the ocular pressure value readouts with appropriate means for automatic or manual "on"/"off" control.

Details and advantages will become more apparent from the following description of the illustrative embodiments when read in conjunction with the accompanying drawings. For simplicity sake, the invention will be described as adapted and/or utilized in conjunction with slit lamp tonometers of the type disclosed in the aforesaid two patents, although adequate alterations will be obvious to those skilled in the art in order to adapt the invention to virtually any type tonometer.

With the above and other objects in view that will herein after appear, the nature of the invention will be more clearly understood by reference to the following detailed description, the appended claims and the several views illustrated in the accompanying drawings.

BRIEF DESCRIPTION OF THE DRAWINGS

FIG. 3 is a schematic side elevational view of another applanation tonometer constructed in accordance with this invention, and illustrates an associated optical system which avoids a diagonal optical path inherent in the optical system of the tonometer of FIGS. 1 and 2.

FIG. 4 is a front view of another applanation tonometer of this invention, and illustrates a tonometer support rod constructed as an optical column housing an optical system of the applanation tonometer.

DESCRIPTION OF THE PREFERRED EMBODIMENTS

Figures 1, 2:
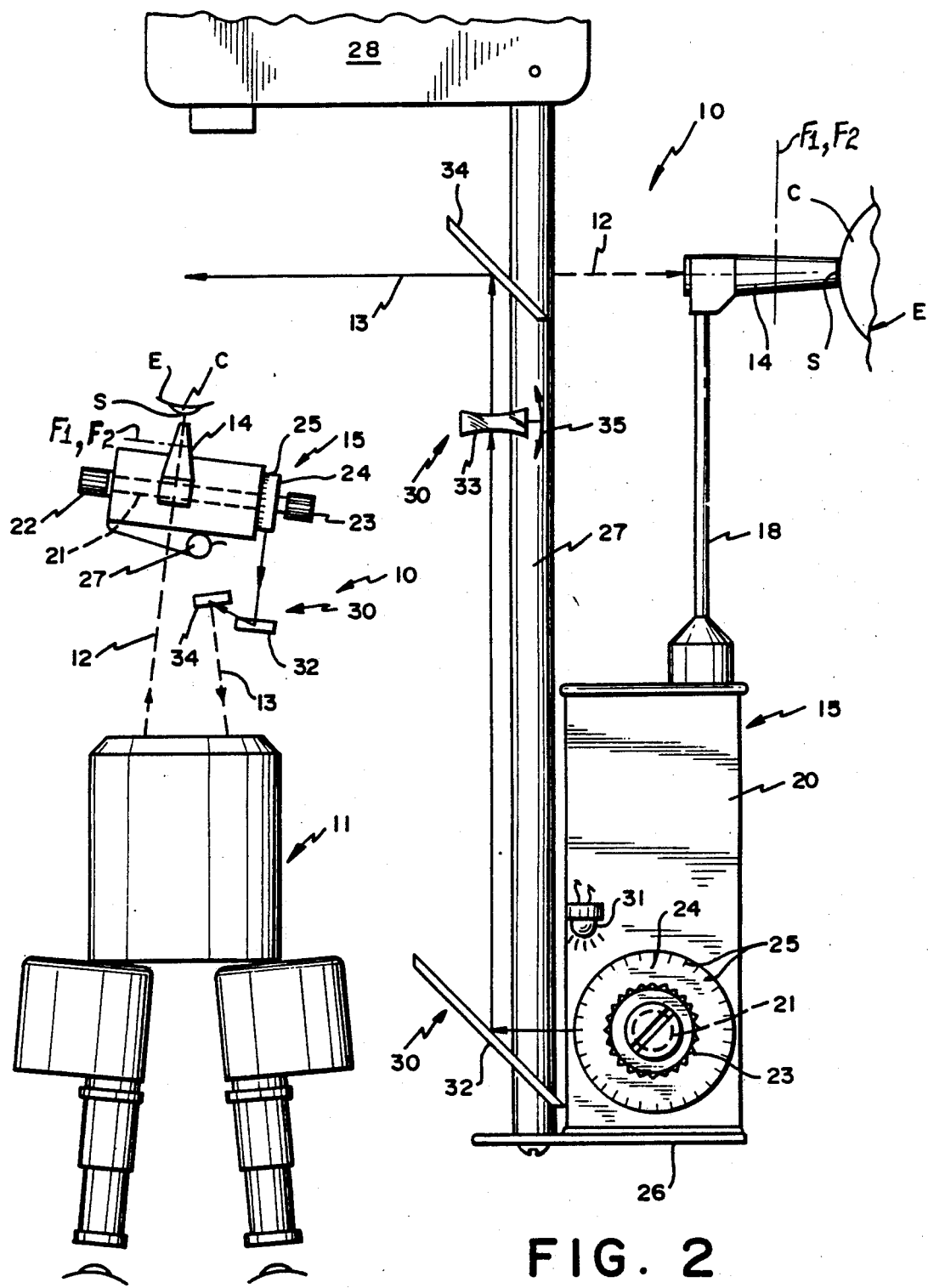
FIG. 1 is a schematic top plan view of a slit lamp tonometer, and illustrates a bimicroscopic head, a tonometer and a tonometer tip, and two mirrors forming part of the present invention which translate, transmit and optically display the image of an associated ocular pressure scale to the focal plane of the heretofore unused half of the bimicroscope.
FIG. 2 is a schematic enlarged side elevational view of the tonometer body of FIG. 1, and illustrates the tonometer tip, a rotary pressure knob having an intraocular pressure scale thereon, and associated prisms, mirrors and lenses of the system for transmitting and displaying the intraocular pressure value of the scale along the heretofore unused half or second viewing axis of the bimicroscope.

A novel slit lamp applanation tonometer constructed in accordance with a first embodiment of the invention is illustrated in FIGS. 1 and 2 of the drawings and is generally designated by the reference numeral 10.

The applanation tonometer 10 utilizes in conjunction therewith a conventional slit lamp bimicroscope 11 provided with conventional internal lens systems for optics defining two optical viewing axes 12, 13 with focal planes F1, F2, respectively, (FIGS. 1 and 2) that closely coincide. However, in the conventional slit lamp bimicroscope 11 only the optical viewing axis 12 of the two optical viewing axes 12, 13 is used to focus on a tonometer tip 14 of a conventional applanation tonometer 15 of the type disclosed in any one of the two latter-noted patents. In the applanation tonometer 10 of the present invention, it is the optical viewing axis 12 along which the ophthalmologist, operator or user of the tonometer 10 utilizes to view the image of a compressed surface S of a cornea C of a patient's eye E. The otherwise conventionally unused optical axis 13 is utilized in conjunction with the present invention to read ocular pressure of the eye E transmitted along the optical viewing axis 13 simultaneously with viewing the corneal surface S along the optical axis 12.

The conventional tonometer 15 includes in addition to the tonometer tip 14 a rod 18, a tonometer body 20 housing therein mechanisms of the type characteristic of U.S. Pat. Nos. 3,470,736 and/or 3,070,997, a shaft 21, finger knobs 22, 23 fixed to the shaft 21 and a rotary scale 24 which is also fixed to the shaft 21 and carries ocular pressure value or indicia 25 thereupon. The tonometer body 20 is fixed to a bracket 26 which is connected to a support arm or rod 27 or to another conventional support bracket 28. The ocular pressure value or indicia 25 upon the rotary scale 24 is preferably numerals reading from 0 to 10 in terms of millimeters of mercury (Hg) of pressure. This calibration is established straightforwardly in a conventional manner, but reference may be made for the specific thereof to U.S. Pat. Nos. 3,470,736 and 3,070,997. Suffice it to say that as the operator rotates one or the other of the finger knobs 22, 23 during applanation of the corneal surface S and views the same through the tonometer tip 14 along the optical viewing axis 12, the rotary scale 24 will be similarly rotated and will eventually indicate by the pressure indicia 25 the intraocular pressure of the eye E. As was noted earlier, the operator in a conventional operation could not simultaneously view along the optical viewing axis 12 and also simultaneously view the indicia 25 and would, thus, necessarily have to cease viewing through the bimicroscope 11 and look at or view the indicia 25 under dim ambient light conditions.

In accordance with the present invention, means generally designated by the reference numeral 30 are provided for displaying the ocular pressure value or indicia 25 along the optical viewing axis 13 whereby both the applanated corneal surface S and the ocular pressure value or indicia 25 can be viewed simultaneously.

The novel displaying, translating and transmitting means 30 includes as part thereof a light source 31 controlled automatically or manually from a suitable power source and supported conventionally adjacent the rotary scale 24 to illuminate the ocular pressure values or indicia 25 thereupon. The indicia 25 is imaged by an optical reflector 32 in the form of a prism or a front surfaced mirror, although a partial transmittance front surfaced mirror is also considered advantageous in keeping with the present invention in order that the ocular pressure indicia 25 can also pass through the mirror 32 and remain visible to the operator outside of the optics (not shown) of the bimicroscope 11. However, whether the mirror 32 is fully reflective or partially transmissive, the ocular pressure indicia 25 is reflected upwardly from the mirrored surface (unnumbered) of the mirror 32, is focused through a double concave or minus lens 33 and is imaged upon and reflected from another mirror or prism 34. The overall focal length of the system 30 is longer than that of the focal length of the optical axis of the bimicroscope 11 and thus the lens 33 must be introduced in the system to properly image (focus) or display the ocular pressure indicia 25 along the optical viewing axis 13. The position of the lens 33 and the curvature thereof will vary depending upon the dioptric power used. Suffice it to say that the proper position and dioptric power will be chosen to obtain a focusable image of the ocular pressure indicia 25 of an acceptable image size at the focal plane (not shown) of the bimicroscope 11. Means 35, for example, may be provided in the form of a screw adjustment for moving the lens 33 to allow precise axial movement and thereby effect accurate focusing of the ocular pressure indicia 25. However, the mirrors or prisms 32, 34 and the lens 33 are so selected, designed and utilized that the image of the indicia 25 reflected upon the mirrored surface of the mirror 32 eventually coincides with the optical axis 13.

Accordingly, as the operator views through the lens system and optics of the bimicroscope 11, the operator's left eye will observe the corneal surface S as he manipulates the knob 22 and/or 23 and the operator's right eye will simultaneously view the ocular pressure indicia 25 with such viewing occuring, of course, along the respective viewing axes 12, 13. Thus, the operator need not remove his eyes from the bimicroscope 11 during applanation of the corneal surface S and can simultaneously achieve exacting applanation and the pressure value display without, of course, being adversely affected by the dim ambient light conditions heretofore noted.

The system 30 of FIGS. 1 and 2 is relatively simple and straightforward and has the advantage of requiring only two optical reflectors (mirrors or prisms) 32, 34 and the single lens 33. However, the lens 33 is required because the focal length of the optical path of the system 30 is different from the focal length of the optical path of the bimicroscope 11, and the former is created in part by the vertical diagonal optical path between the mirrored surfaces of the mirrors 32, 34 which are offset laterally from each other, as is shown in FIG. 1. This diagonal optical path can be resolved into vertical and horizontal optical paths in keeping with another aspect of the present invention which is illustrated in FIG. 3 in which like part have been provided with like, though primed, reference numerals. In keeping with the invention of FIG. 3, a conventional tonometer 15' having a tip 14' is provided through which an operator views along an optical viewing axis 12' of the bimicroscope (not shown, but 11 of FIG. 1). As in the case of the translating, transmitting and displaying means or system 30 of FIGS. 1 and 2, the like means or system 30' includes a fully reflective or partially transmissive mirror or prism 32', a double concave or minus lens 33' and a mirror or prism 34'. However, the mirror 34' is not vertically diagonally offset from the mirror 32' but is instead vertically aligned therewith and unless otherwise provided for the image reflected from the mirrored surface of the mirror 34' would not be coincident with the optical viewing axis 13' of the bimicroscope. Accordingly, prisms 40, 41 (or comparable mirrors) are arranged relative to each other and to the mirror or prism 34' such as to coincide the pressure value indicia image along the optical viewing axis 13'.

In the slit lamp tonometers 10 and 10', it is to be understood that if the images of the corneal surface S along the optical viewing axis 12' and the ocular pressure indicia 25 viewed along the optical viewing axis 13' fall upon a common focal plane, the two images are centered or overlapped. However, by slightly cocking the mirror 34 and/or adjusting the mirrors or prisms 40, 41, the image reflected therefrom would be still generally along the optical viewing axis 13, 13', respectively, but obviously just slightly offset therefrom. In this manner, the images of the corneal surface S and the ocular pressure indicia 25 would not be coincident or on top of each other but instead would be offset or in side-to-side relationship thereby rendering clear image of each.

Reference is now made to FIG. 4 which illustrates another cslit lamp tonometer 10" which includes elements generally structurally and functionally identical to those of the tonometers 10, 10' and, hence, have been double primed. In keeping with the slit lamp tonometers 10, 10' of FIGS. 1, 2 and 3, respectively, the translating, transmitting and display systems 30, 30', respectively, have been described as being suitably mounted/supported by appropriate means (not shown) relative to the tonometer bodies 15, 15' and the bimicroscopes 11, 11'. For example, the lamp 31, 31', the mirrors or prisms 32, 32' and 34, 34' and the lenses 33, 33' including the adjusting means 35 can be suitably carried by a common support connected in a conventional manner to the tonometer body 15, 15' or to the support rod 27 or 27'. However, in tonometers using support rods this arrangement can prove difficult to accomplish in that conventional support rods 27, 27' used with conventional tonometer bodies 15, 15' are often positioned such that they partially obscure the visual field of the optical viewing axis 13, as is representative of FIG. 1. In such cases it is advantageous to replace the solid support rods 27, 27' with another support rod 27" (FIG. 4) which is of a generally tubular hollow configuration having a cylindrical upright portion 45 and a lateral portion 46 collectively defining a hollow interior chamber 47. The lateral portion 46 is located contiguous the lamp 31" and the indicia 25" of the rotary scale 24". Mirrors or prisms 32", 34" and a lens 33" adjusted vertically by conventional means 35" are all appropriately housed within the chamber 47. Obviously, the support rod 27" has an opening (not shown) therein from which light reflected from the mirror 34" will exit the support rod 27" along the optical viewing axis (not shown, but 13, 13' of FIGS. 1, 2 and 3.) In this manner the standard support rod 27 of a conventional tonometer 15, 15' can be removed and replaced by the support rod 27" and the translating, transmitting and displaying means 30" thereof. The only additional requirement of the overall system 30" is the inclusion of another prism or mirror 48 for reflecting the ocular pressure indicia 25" from the rotary scale 24" at right angles to the prism 32".

It should also be appreciated that the optics of the translating, transmitting and display systems 30, 30' and/or 30" can as well be achieved by fiberoptical systems so long as necessary focusing lenses are utilized.

Figure 5:
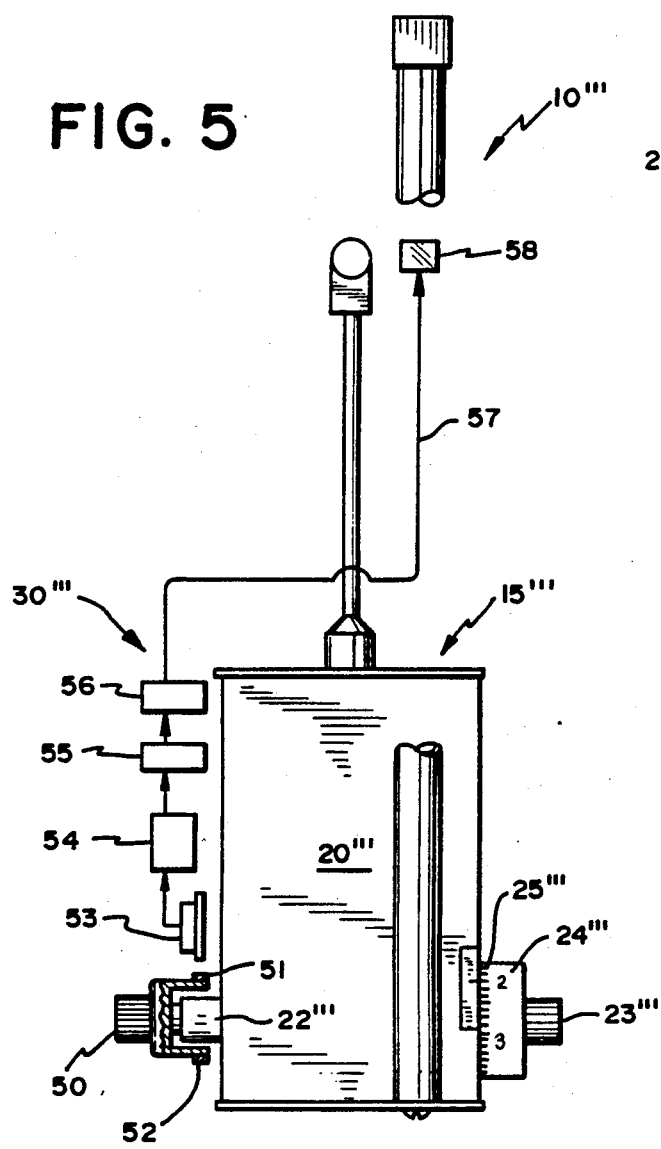
FIG. 5 is a schematic front view of another applanation tonometer of the present invention, and illustrates an electronic/electrical system for converting pressure knob rotation into digital ocular pressure values or numerals displayed along the heretofore unused o second viewing axis of the bimicroscope.

Another slit lamp tonometer 10''' which includes a conventional tonometer 15''' and its like triple primed component is illustrated in FIG. 5 of the drawings and is designed primarily to convert analog movements of the rotary scale 24''' into digital numerals representing the ocular pressure indicia 25'''. An adapter 50 is conventionally screwed or otherwise fixed to the knob 22''' or alternatively the knob 22''' is removed and the adapted 50 is conventionally fixed to the shaft (not shown) corresponding to the shaft 21 of the tonometer 10 (FIG. 1). The adapter 50 carries a plurality of magnets 51, 52, etc. spaced about the circumference with, for example, one magnet associated with each 10 millimeters of pressure or a total of eight (8) magnets 51, 52, etc. The circumferential array of magnets 51, 52, etc. are aligned with a sensor 53 which is preferably a Hall effect sensor, such as the Sprague 3020. Impulses created by the magnets 51, 52, etc. during the rotation of the adapter 50 are sensed by the sensor 53 and signals are conducted to a conventional analog to digital converter 54, to a conventional reversible counter 55, to a decoder 56, and by electric circuitry 57 to a liquid crystal display (LCD) or a light-emitting dial display 58 imaged in coincidence with the axis 13 (See FIGS. 1 and 2). This digital data of the ocular pressure value might require a positive lens (not shown) if placed proximal to the focal plane of the bimicroscope 11. However, the translating, transmitting and displaying system 30''' is essentially nonoptic until utilization of the liquid crystal display o the light-emitting dial display 58 and, thus, affords a greater degree of latitude and engineering application because of the absence of numerous optical paths and the singular requirement that the display 58 be generally coincident with the optical viewing axis 13. Accordingly, virtually the entire system or means 30''' can be housed within the tonometer body 20''', and in such a case the magnets 51, 52, etc. would simply be mounted upon the shaft 21 (FIG. 1). A conventional system for such numeric display utilizing Hall effect sensing is fully disclosed in U.S. Pat. No. 4,807,265 in the name of Carl S. Swanson which granted on Feb. 21, 1989 and is incorporated completely herein by reference. Alternatively, numerous other methods/apparatus of analog to digital conversion are available which could similarly be incorporated onto or into the tonometer. It is appreciated that the system 30'''' may also incorporate an optical path utilizing mirrors or fiber optics and any necessary focusing lens should the digital display be more conventionally placed in the tonometer body rather than being supported at the level of optical axis 12.

Figure 6:
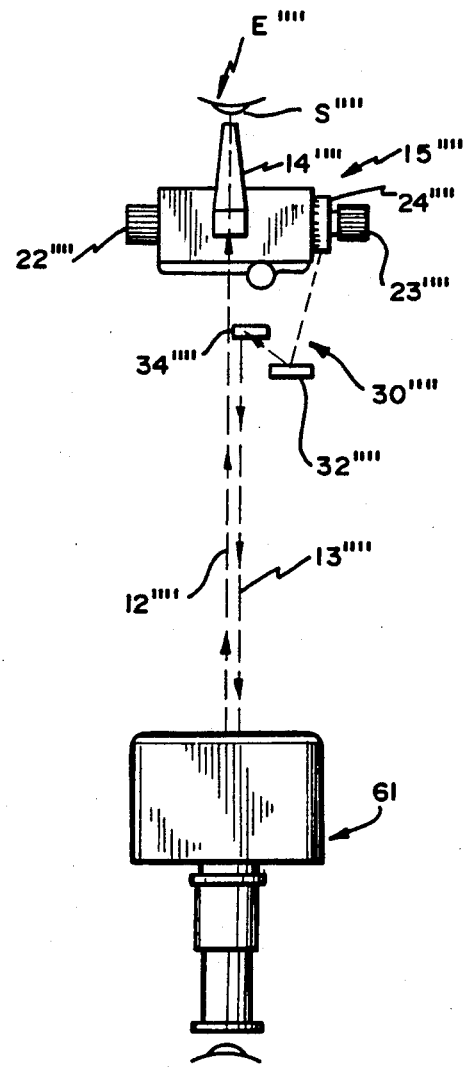
FIG. 6 is a top plan view of a slit lamp tonometer utilizing a microscope head, and illustrates a lens system similar to FIG. 1 but which transmits the ocular pressure value along generally the same viewing axis as that used by an operator to view the compressed corneal surface.

A final applanation tonometer constructed in accordance with this invention is illustrated in FIG. 6 and is generally designated by the reference numeral 10'''' with identical elements corresponding to those of the tonometer 10 being like quadruple primed. In this case, the slit lamp tonometer 10'''' includes a conventional applanation tonometer 15'''' but instead of the bimicroscope 11, the slit lamp tonometer includes a microscope 61 having a focal plane and a single lens system (not shown) defining a single optical viewing axis 12'''' along which the corneal surface S'''' of an eye E'''' can be viewed through a tonometer tip 14'''' . Obviously, the viewing axis 13 of the bimicroscope 11 of FIG. 1 is nonexistent in the microscope 61 and, thus, the light rays reflected by the mirrors 32'''', 34'''' and the lens (not shown but corresponding to the lens 33) is refocused along an axis 13'''' which is virtually coincident to the axis 12''''. The axes 12'''' and 13'''' are shown spaced a considerable distance from each other in FIG. 6, but this distance is extremely small and virtually nonexistant so that both the image of the corneal surface S'''' and the image of the ocular pressure indicia 25'''' can be both displayed on a single focal plane of the microscope 61 and, thus, be viewed simultaneously. Mirror 34'''' may be partially reflective and partially transmissive and thus transmit both optical viewing axes 12'''', 13'''' to facilitate simultaneous viewing.

In keeping with the various aspects of the inventions heretofore described, all of the translating, transmitting and display systems 30, 30', etc. are preferably self-illuminated through conventional miniature lamps, light-emitting diodes and back-lit LED displays, the latter particularly in conjunction with the embodiment of the invention of FIG. 5. Such illumination allows variable intensity so that the ocular pressure indicia illumination can be adjusted to match that of the bright green semicircles of the tonometer tip image of the corneal surface S. The electrical power for the illumination or for the electrical digital systems may be obtained from either the slit lamp power source (not shown) or from separate batteries. Preferably means (not shown) are provided by which the lamps 31, 31' are activated only when the tonometers 15, 15' etc. are properly positioned for use, and are automatically deactivated when the tonometers are removed from their position of use.

Although a preferred embodiment of the invention has been specifically illustrated and described herein, it is to be understood that minor variations may be made in the apparatus without departing from the spirit and scope of the invention, as defined in the appended claims.

I claim:

1. An applanation tonometer comprising a tonometer tip for contacting a surface of a cornea of an eye, means for moving the tonometer tip to applanate and vary the degree of applanation of the corneal surface, means for establishing an optical viewing axis along which the applanated corneal surface can be viewed, means for transforming the degree of applanation to an ocular pressure value, and means for displaying the ocular pressure value at a location at which it is visible when a user views along said optical viewing axis whereby both the applanated corneal surface and the ocular pressure value thereof can be viewed simultaneously.

2. The applanation tonometer as defined in claim 1 wherein said optical viewing axis establishing means establishes first and second viewing axes, said applanated corneal surface is viewed along said first optical viewing axis, and said ocular pressure value is viewed along said second optical viewing axis.

3. The applanation tonometer as defined in claim 2 wherein the means for establishing is a bimicroscope and the location at which the ocular pressure value is visible is a focal plane of said bimicroscope.

4. The applanation tonometer as defined in claim 1 wherein said optical viewing axis establishing means establishes first and second viewing axes, said applanated corneal surface is viewed along said first optical viewing axis, said ocular pressure value is viewed along said second optical viewing axis, and said optical viewing axis establishing means is a slit lamp bimicroscope.

5. The applanation tonometer as defined in claim 1 wherein said optical viewing axis establishing means establishes first and second viewing axes, said applanated corneal surface is viewed along said first optical viewing axis by a user's first eye, and said ocular pressure value is viewed along said second optical viewing axis by a user's second eye.

6. The applanation tonometer as defined in claim 1 wherein said optical viewing axis establishing means establishes first and second viewing axes, said applanated corneal surface is viewed along said first optical viewing axis, said ocular pressure value is viewed along said second optical viewing axis, and both said first and second viewing axes are viewed by a single eye of a user.

7. The applanation tonometer as defined in claim 1 wherein said displaying means includes means for electronically transmitting the ocular pressure value from the transforming means to the location at which it is visible during user viewing along said optical viewing axis.

8. The applanation tonometer as defined in claim 1 wherein said displaying means includes means for optically transmitting the ocular pressure value from the transforming means to the location at which it is visible during user viewing along said optical viewing axis.

9. The applanation tonometer as defined in claim 1 wherein the means for establishing is a bimicroscope and the location at which the ocular pressure value is visible is a focal plane of said bimicroscope.

10. The applanation tonometer as defined in claim 1 wherein the means for establishing is a microscope and the location at which the ocular pressure valve is visible is a focal plane of said microscope.

11. The applanation tonometer as defined in claim 1 wherein said optical viewing axis establishing means establishes first and second viewing axes, said applanated corneal surface is viewed along said first optical viewing axis, said ocular pressure value is viewed along said second optical viewing axis, said first and second optical viewing axes are virtually coincident, and both said first and second viewing axes are viewed by a single eye of a user.

12. The applanation tonometer as defined in claim 1 wherein said displaying means includes means for electronically and optically transmitting the ocular pressure value from the transforming means to the location at which it is visible during user viewing along said optical viewing axis.

* * * * *